United States Patent
Day et al.

(10) Patent No.: US 9,724,470 B2
(45) Date of Patent: Aug. 8, 2017

(54) SYSTEM FOR MONITORING AND DELIVERING MEDICATION TO A PATIENT AND METHOD OF USING THE SAME TO MINIMIZE THE RISKS ASSOCIATED WITH AUTOMATED THERAPY

(71) Applicant: ICU Medical, Inc., San Clemente, CA (US)

(72) Inventors: William Kenneth Day, Hoffman Estates, IL (US); Timothy L. Ruchti, Gurnee, IL (US)

(73) Assignee: ICU Medical, Inc., San Clemente, CA (US)

(*) Notice: Subject to any disclaimer, the term of this patent is extended or adjusted under 35 U.S.C. 154(b) by 0 days.

(21) Appl. No.: 14/739,840

(22) Filed: Jun. 15, 2015

(65) Prior Publication Data
US 2015/0359966 A1 Dec. 17, 2015

Related U.S. Application Data

(60) Provisional application No. 62/012,756, filed on Jun. 16, 2014.

(51) Int. Cl.
G08B 21/00 (2006.01)
A61M 5/172 (2006.01)
(Continued)

(52) U.S. Cl.
CPC ........... *A61M 5/1723* (2013.01); *A61M 5/365* (2013.01); *A61M 2005/14208* (2013.01);
(Continued)

(58) Field of Classification Search
CPC . A61B 5/00; A61M 1/00; A61M 5/00; A61M 5/142; A61M 5/166; A61M 5/172; A61M 31/00; G06F 19/00
(Continued)

(56) References Cited

U.S. PATENT DOCUMENTS 5,153,827 A 10/1992 Coutre et al.
5,697,899 A 12/1997 Hillman et al.
(Continued)

FOREIGN PATENT DOCUMENTS

EP 1500025 B1 4/2003
EP 2228004 A1 9/2010
(Continued)

OTHER PUBLICATIONS

Cannon et al, "Automated Heparin-Delivery System to Control Activated Partial Thromboplastin Time", Circulation 99:751-756 (1999).
(Continued)

*Primary Examiner* — Eric M Blount
(74) *Attorney, Agent, or Firm* — Knobbe Martens Olson & Bear, LLP

(57) ABSTRACT

A system and method for monitoring and delivering medication to a patient. The system includes a controller that has a control algorithm and a closed loop control that monitors the control algorithm. A sensor is in communication with the controller and monitors a medical condition. A rule based application in the controller receives data from the sensor and the closed loop control and compares the data to predetermined medical information to determine the risk of automation of therapy to the patient. A system monitor is also in communication with the controller to monitor system, remote system, and network activity and conditions. The controller then provides a predetermined risk threshold where below the predetermined risk threshold automated closed loop medication therapy is provided. If the predetermined risk threshold is met or exceeded, automated therapy adjustments may not occur and user/clinician intervention is requested.

14 Claims, 5 Drawing Sheets

(51) Int. Cl.
    *A61M 5/36*         (2006.01)
    *A61M 5/168*       (2006.01)
    *A61M 5/142*       (2006.01)

(52) U.S. Cl.
    CPC ............ *A61M 2005/16863* (2013.01); *A61M 2205/16* (2013.01); *A61M 2205/18* (2013.01); *A61M 2205/3553* (2013.01)

(58) Field of Classification Search
    USPC .......................................... 340/540; 604/506
    See application file for complete search history.

(56) References Cited

U.S. PATENT DOCUMENTS

| | | |
|---|---|---|
| 5,800,387 A | 9/1998 | Duffy et al. |
| 5,885,245 A | 3/1999 | Lynch et al. |
| 5,920,263 A | 7/1999 | Huttenhoff et al. |
| 6,017,318 A | 1/2000 | Gauthier et al. |
| 7,267,664 B2 | 9/2007 | Rizzo |
| 7,354,420 B2 | 4/2008 | Steil et al. |
| 7,369,948 B1 | 5/2008 | Ferenczi et al. |
| 7,398,183 B2 | 7/2008 | Holland et al. |
| 7,402,153 B2 | 7/2008 | Steil et al. |
| 7,785,313 B2 | 8/2010 | Mastrototaro |
| 7,806,886 B2 | 10/2010 | Kanderian, Jr. et al. |
| 7,826,981 B2 | 11/2010 | Goode, Jr. et al. |
| 8,149,131 B2 | 4/2012 | Blomquist |
| 8,518,021 B2 | 8/2013 | Stewart et al. |
| 8,543,416 B2 | 9/2013 | Palmroos et al. |
| 2002/0077852 A1 | 6/2002 | Ford |
| 2003/0009244 A1 | 1/2003 | Engleson |
| 2003/0050621 A1 | 3/2003 | Lebel et al. |
| 2003/0060688 A1 | 3/2003 | Ciarniello et al. |
| 2003/0141981 A1 | 7/2003 | Bui |
| 2003/0204416 A1 | 10/2003 | Radpay |
| 2004/0167465 A1 | 8/2004 | Mihai |
| 2004/0167804 A1 | 8/2004 | Simpson |
| 2004/0172283 A1 | 9/2004 | Vanderveen |
| 2004/0193325 A1 | 9/2004 | Bonderud |
| 2005/0038680 A1 | 2/2005 | McMahon |
| 2005/0055242 A1 | 3/2005 | Browne |
| 2005/0099624 A1 | 5/2005 | Staehr |
| 2005/0107923 A1 | 5/2005 | Vanderveen |
| 2005/0171503 A1 | 8/2005 | Van Den Berghe et al. |
| 2005/0171815 A1 | 8/2005 | Vanderveen |
| 2005/0224083 A1 | 10/2005 | Crass |
| 2005/0240305 A1 | 10/2005 | Bogash et al. |
| 2005/0273059 A1 | 12/2005 | Mernoe et al. |
| 2006/0047538 A1 | 3/2006 | Condurso et al. |
| 2006/0200007 A1 | 9/2006 | Brockway et al. |
| 2006/0265246 A1 | 11/2006 | Hoag |
| 2007/0156452 A1 | 7/2007 | Batch |
| 2007/0233035 A1 | 10/2007 | Wehba et al. |
| 2007/0257788 A1 | 11/2007 | Carlson |
| 2008/0009684 A1 | 1/2008 | Corsetti et al. |
| 2008/0188796 A1 | 8/2008 | Steil et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro |
| 2009/0054754 A1 | 2/2009 | McMahon et al. |
| 2009/0177146 A1* | 7/2009 | Nesbitt ............ A61M 5/14228 604/66 |
| 2010/0022988 A1 | 1/2010 | Wochner |
| 2010/0036310 A1 | 2/2010 | Hillman |
| 2010/0056992 A1 | 3/2010 | Hayter |
| 2010/0121170 A1 | 5/2010 | Rule |
| 2010/0121654 A1 | 5/2010 | Portnoy et al. |
| 2010/0160854 A1 | 6/2010 | Gauthier |
| 2010/0198034 A1 | 8/2010 | Thomas et al. |
| 2010/0212675 A1 | 8/2010 | Walling et al. |
| 2010/0217621 A1 | 8/2010 | Schoenberg |
| 2010/0273738 A1 | 10/2010 | Valcke et al. |
| 2010/0298765 A1* | 11/2010 | Budiman ............ A61B 5/14532 604/66 |
| 2010/0318025 A1* | 12/2010 | John ................ A61M 25/0026 604/84 |
| 2011/0099313 A1 | 4/2011 | Bolanowski |
| 2011/0175728 A1 | 7/2011 | Baker, Jr. |
| 2011/0320049 A1 | 12/2011 | Chossat |
| 2013/0006666 A1 | 1/2013 | Schneider |
| 2013/0158504 A1* | 6/2013 | Ruchti ................ A61M 5/1723 604/504 |
| 2013/0291116 A1 | 10/2013 | Homer |
| 2013/0296823 A1 | 11/2013 | Melker et al. |
| 2013/0296984 A1 | 11/2013 | Burnett et al. |
| 2014/0039446 A1 | 2/2014 | Day |

FOREIGN PATENT DOCUMENTS

| | | |
|---|---|---|
| EP | 2243506 A2 | 10/2010 |
| WO | 96/25186 A2 | 8/1996 |
| WO | 02/05702 A2 | 1/2002 |
| WO | 2004/060455 A1 | 7/2004 |
| WO | 2005/057175 A2 | 6/2005 |
| WO | 2007/087443 A2 | 8/2007 |
| WO | 2008/067245 A2 | 6/2008 |
| WO | 2008/088490 A1 | 7/2008 |
| WO | 2008/134146 A1 | 11/2008 |
| WO | 2009/016504 A2 | 2/2009 |
| WO | 2009/023406 A1 | 2/2009 |
| WO | 2009/023407 A1 | 2/2009 |
| WO | 2009/049252 A1 | 4/2009 |
| WO | 2010/017279 A1 | 2/2010 |
| WO | 2010/075371 A1 | 7/2010 |
| WO | 2010/099313 A1 | 9/2010 |
| WO | 2010/114929 A1 | 10/2010 |
| WO | 2010/119409 A1 | 10/2010 |
| WO | 2010/124127 A1 | 10/2010 |
| WO | 2010/135646 A1 | 11/2010 |
| WO | 2010/135654 A2 | 11/2010 |
| WO | 2010/135686 A2 | 11/2010 |

OTHER PUBLICATIONS

Mauseth et al, "Proposed Clinical Application for Tuning Fuzzy Logic Controller of Artificial Pancreas Utilizing a Personalization Factor", Journal of Diabetes Science and Technology 4(4):913-922 (2010).

Pretty et al, "Hypoglycemia Detection in Critical Care Using Continuous Glucose Monitors: An in Silico Proof of Concept Analysis", Journal of Diabetes Science and Technology 4(1):15-24 (2010).

Zakarian et al, "Combination of biphasic transmittance waveform with blood procalcitonin levels for diagnosis of sepsis in acutely ill patients", Critical Care Medicine 36(5)1507-1512 (2008).

* cited by examiner

SYSTEM FOR MONITORING AND DELIVERING MEDICATION TO A PATIENT AND METHOD OF USING THE SAME TO MINIMIZE THE RISKS ASSOCIATED WITH AUTOMATED THERAPY

BACKGROUND OF THE INVENTION

This invention relates to a system for monitoring and delivering medication to a patient. More specifically, the present invention is directed toward a device that monitors the risk to a patient of an automated therapy decision and allows a clinician to customize rules that determine whether an automated change in therapy is to be allowed or whether user/clinician intervention should be required based upon the risk of automation and the customized rules.

Diabetes is a metabolic disorder that afflicts tens of millions of people throughout the world. Diabetes results from the inability of the body to properly utilize and metabolize carbohydrates, particularly glucose. Normally, the finely tuned balance between glucose in the blood and glucose in bodily tissue cells is maintained by insulin, a hormone produced by the pancreas which controls, among other things, the transfer of glucose from blood into body tissue cells. Upsetting this balance causes many complications and pathologies including heart disease, coronary and peripheral artery sclerosis, peripheral neuropathies, retinal damage, cataracts, hypertension, coma, and death from hypoglycemic shock.

In patients with insulin-dependent diabetes the symptoms of the disease can be controlled by administering additional insulin (or other agents that have similar effects) by injection or by external or implantable insulin pumps. The correct insulin dosage is a function of the level of glucose in the blood. Ideally, insulin administration should be continuously readjusted in response to changes in blood glucose level. In diabetes management, insulin enables the uptake of glucose by the body's cells from the blood. Glucagon acts opposite to insulin and causes the liver to release glucose into the blood stream. The basal rate is the rate of continuous supply of insulin provided by an insulin delivery device (pump). The bolus is the specific amount of insulin that is given to raise blood concentration of the insulin to an effective level when needed (as opposed to continuous).

Presently, systems are available for continuously monitoring blood glucose levels by inserting a glucose sensitive probe into the patient's subcutaneous layer or vascular compartment or, alternately, by periodically drawing blood from a vascular access point to a sensor. Such probes measure various properties of blood or other tissues including optical absorption, electrochemical potential, and enzymatic products. The output of such sensors can be communicated to a hand held device that is used to calculate an appropriate dosage of insulin to be delivered into the blood stream in view of several factors such as a patient's present glucose level and rate of change, insulin administration rate, carbohydrates consumed or to be consumed, steroid usage, renal and hepatic status and exercise. These calculations can then be used to control a pump that delivers the insulin either at a controlled basal rate or as a periodic or one-time bolus. When provided as an integrated system the continuous glucose monitor, controller, and pump work together to provide continuous glucose monitoring and insulin pump control.

Such systems at present require intervention by a patient or clinician to calculate and control the amount of insulin to be delivered. However, there may be periods when the patient is not able to adjust insulin delivery. For example, when the patient is sleeping he or she cannot intervene in the delivery of insulin yet control of a patient's glucose level is still necessary. A system capable of integrating and automating the functions of glucose monitoring and controlled insulin delivery would be useful in assisting patients in maintaining their glucose levels, especially during periods of the day when they are unable to intervene.

Alternately, in the hospital environment an optimal glucose management system involves frequent adjustments to insulin delivery rates in response to the variables previously mentioned. However, constant intervention on the part of the clinician is burdensome and most glucose management systems are designed to maximize the time interval between insulin updates. A system capable of safely automating low-risk decisions for insulin delivery would be useful in improving patient insulin therapy and supporting clinician workflow.

Since the year 2000 at least five continuous or semi-continuous glucose monitors have received regulatory approval. In combination with continuous subcutaneous insulin infusion (CSII), these devices have promoted research toward closed loop systems which deliver insulin according to real time needs as opposed to open loop systems which lack the real time responsiveness to changing glucose levels. A closed loop system, also called the artificial pancreas, consists of three components: a glucose monitoring device such as a continuous glucose monitor (CGM) that measures subcutaneous glucose concentration (SC); a titrating algorithm to compute the amount of analyte such as insulin and/or glucagon to be delivered; and one or more analyte pumps to deliver computed analyte doses subcutaneously. Several prototype systems have been developed, tested, and reported based on evaluation in clinical and simulated home settings. This concerted effort promises accelerated progress toward home testing of closed loop systems.

Similarly, closed loop systems have been proposed for the hospital setting and investigational devices have been developed and tested, primarily through animal studies. In addition, several manufacturers are either in the process of developing or have submitted to the FDA automated glucose measurement systems designed for inpatient testing. Such systems will accelerate the development of fully automated systems for inpatient glucose management.

The primary problem with closed loop control or full automation of insulin therapy is that a computerized system makes decisions that may be high risk in terms of potential consequences if the patient's condition changes or differs from the assumptions behind the computerized decision system. As a result of the automation these high risk decisions are not uncovered until the risk is realized and the patient displays an unacceptable medical condition. Second, in the event of a device failure or medication management system or MMS failure, action is required by the automated system despite the potential lack of information. Third, in scenarios in which frequent glucose measurements are automatically collected but automation is not desired, it is undesirable to update the infusion at the same frequency as glucose measurements are collected. Fourth, when user intervention is required it may be undesirable or difficult for a clinician to respond at the bedside. For example, if the patient is in an isolation room but is observable the clinician may desire to update the infusion rate without entering the room.

Thus, a principle object of the invention is to provide an improved system for monitoring and delivering medication to a patient that makes risk determinations before providing therapy.

Another object of the invention is to provide a system that minimizes patient risk by mapping device failure, patient state and condition, and uncertainty.

Yet another object of the invention is to provide a system for monitoring and delivering medication to a patient that minimizes the risk to a patient.

Another object of the invention is to provide a system for monitoring and delivering medication that is able to selectively request for a user intervention.

These and other objects, features, or advantages of the invention will become apparent from the specification and claims.

BRIEF SUMMARY OF THE INVENTION

A system for monitoring and delivering medication to a patient and the method of using the same. The system has a controller that has an adjustment or control algorithm and an automation risk monitor that monitors the control algorithm. More specifically, the present invention is directed toward a system and method that monitors the risk to a patient of an automated therapy decision and allows a clinician to customize rules that determine whether an automated change in therapy is to be allowed or whether user/clinician intervention should be required based upon the risk of automation and the customized rules. Thus, the risk of potential adverse consequences to the patient if the patient's condition changes or differs from the assumptions behind the computerized or automated decision system can be minimized.

A sensor in communication with the controller monitors a medical condition to provide data to a rule based application in the controller. In addition, the rule based application receives data from the closed loop control and compares the data to predetermined medical information to determine the risk to the patient. When the risk is below a predetermined risk threshold, medication or therapy adjustments are allowed to occur in an automated manner according to a closed loop algorithm. Alternatively, when the risk is above the predetermined risk threshold, the controller triggers a request for user intervention or reduces the degree of automated therapy allowed.

A system monitor in communication with the controller monitors conditions and activity of the system and remote system. Upon detection of a system failure the system monitor provides data to the controller to determine whether to adjust treatment, message a clinician, and send an alarm. Similarly, the system monitor tracks network activity to detect network failures or failures of remote systems such as a clinician messaging system. Depending on the conditions presented an alarm system escalates the alarm sent.

DETAILED DESCRIPTION OF THE PREFERRED EMBODIMENT

Figure 1:
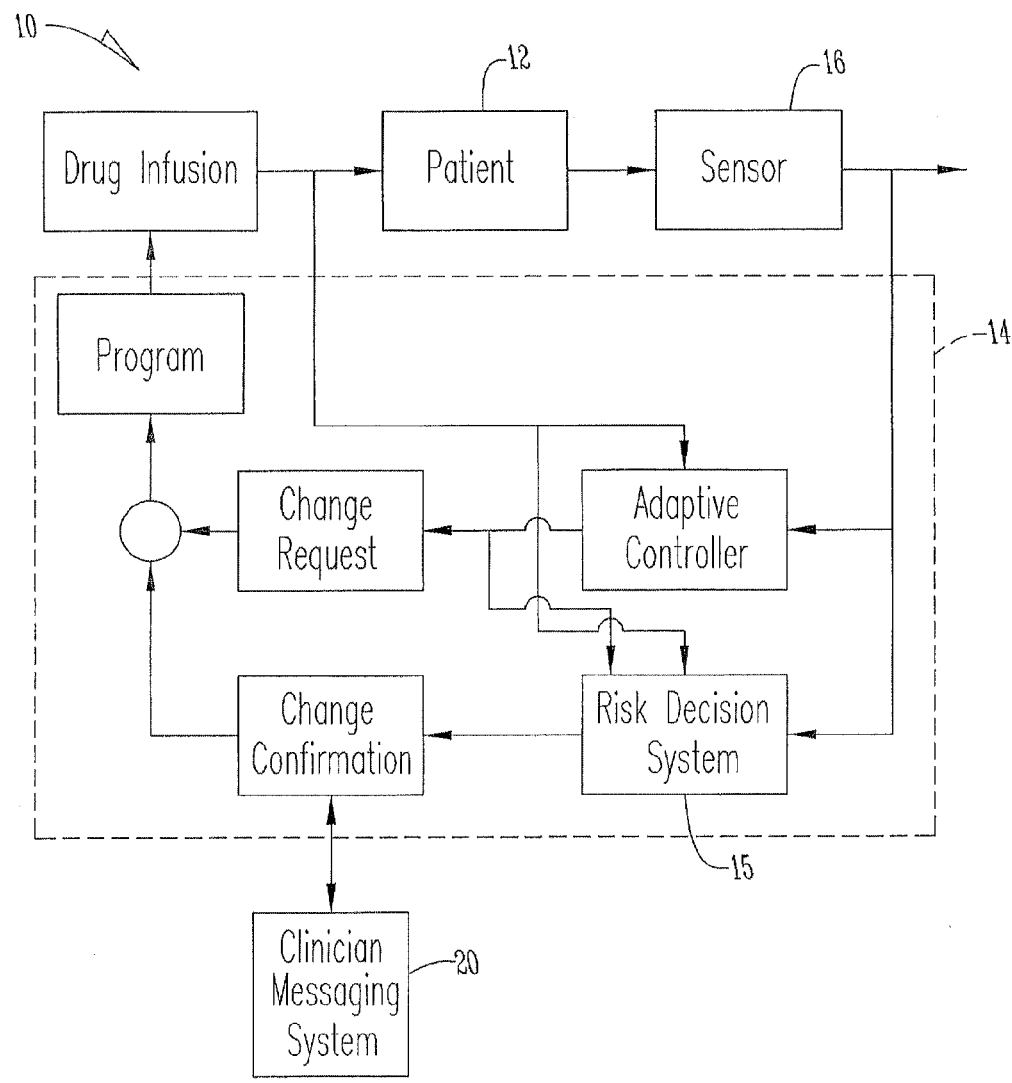
FIG. 1 is a schematic diagram of a closed loop control system augmented with the automation risk monitor of the invention.
Figure 2:
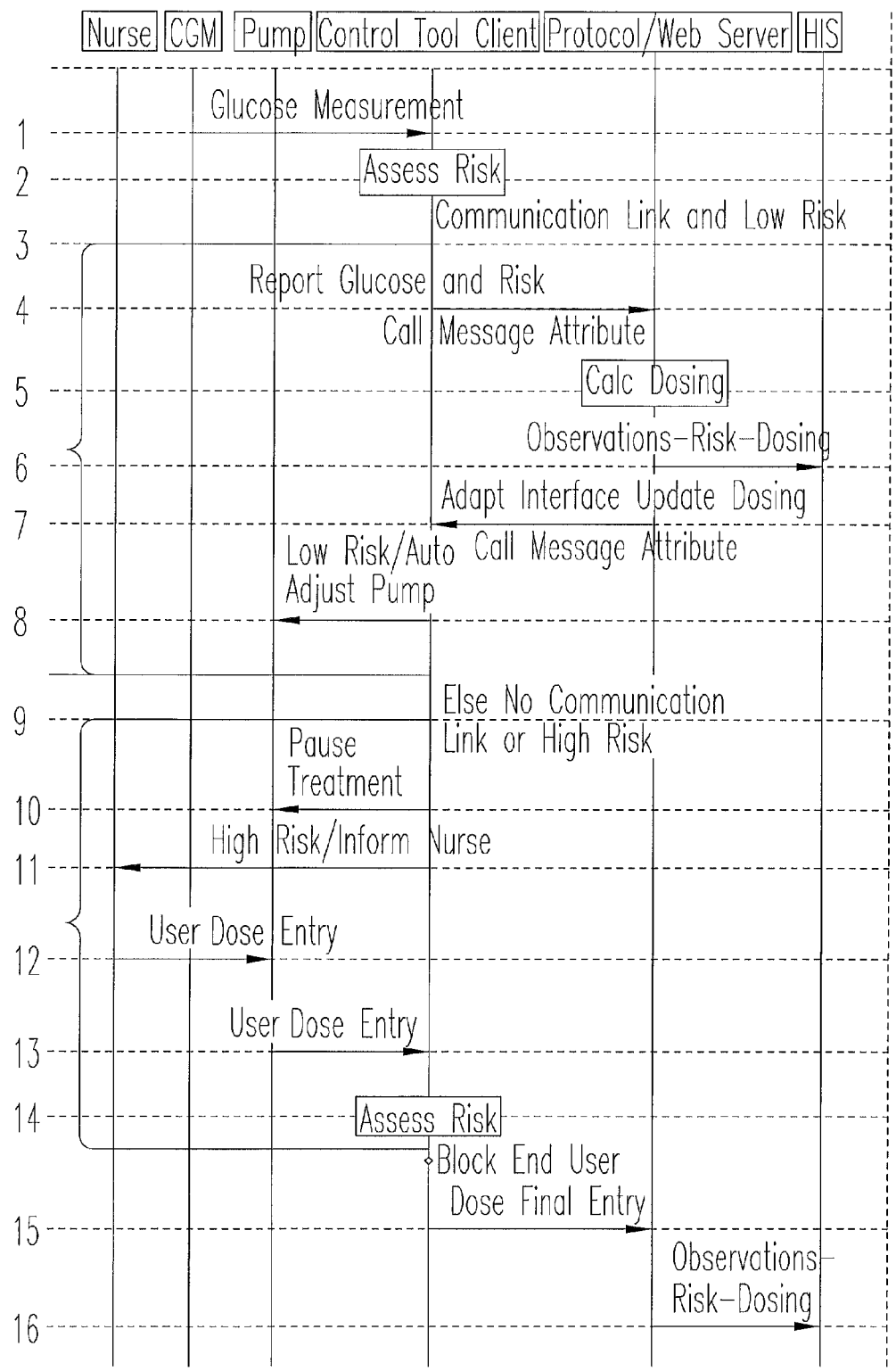
FIG. 2 is an example messaging diagram for the invention.
Figure 3:
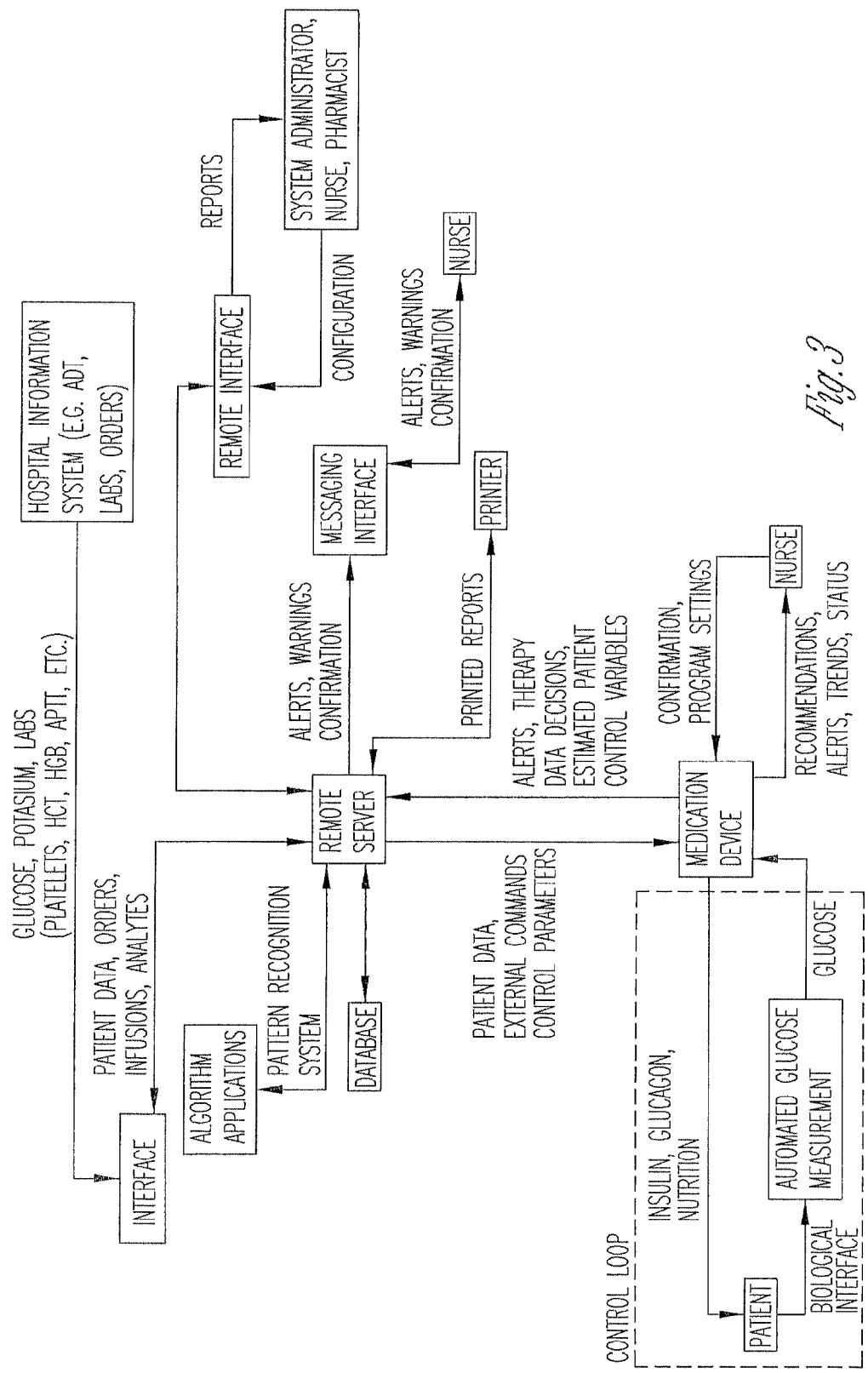
FIG. 3 is a schematic diagram showing the architecture of a semi automatic glucose management system.
Figure 4:
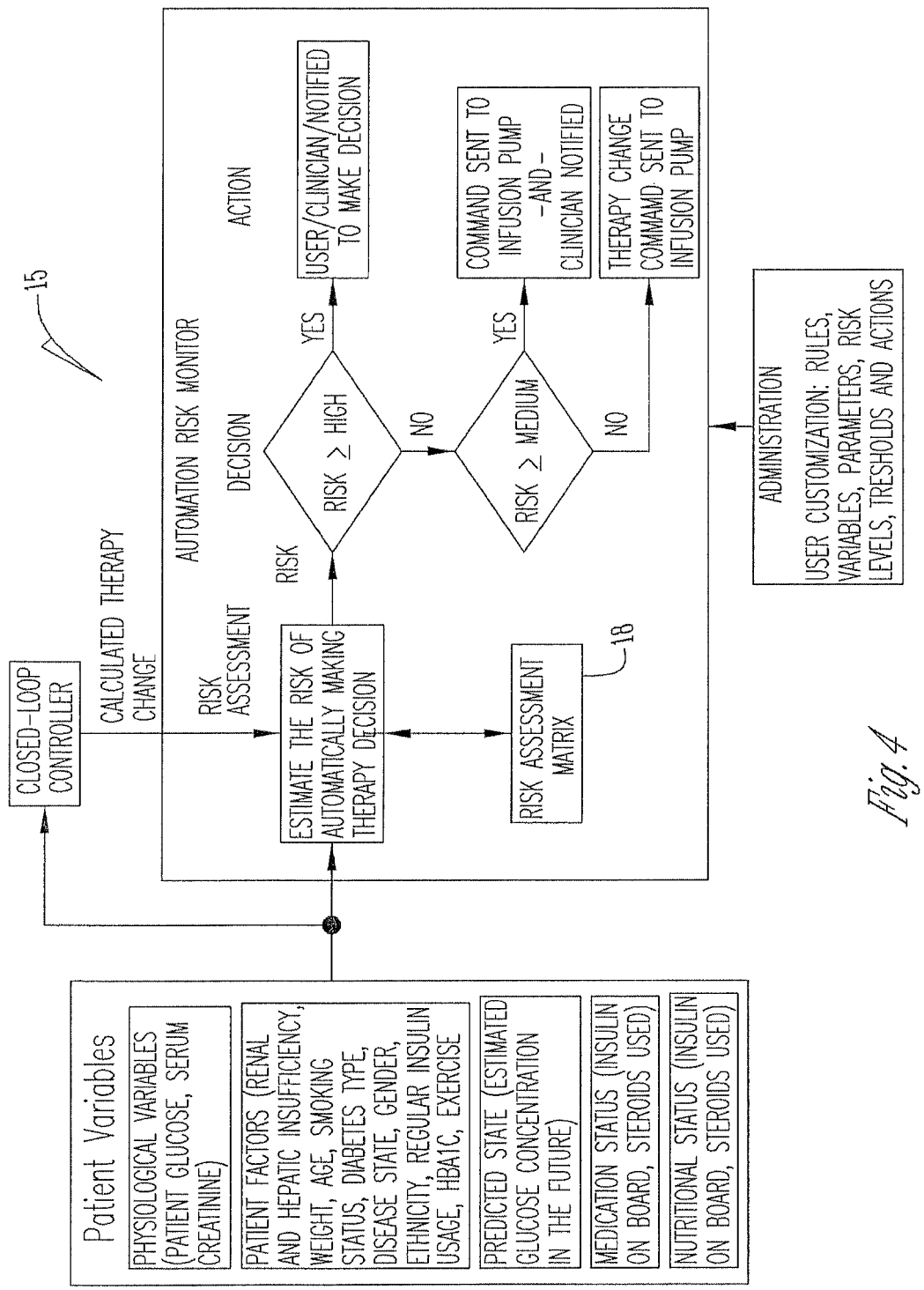
FIG. 4 is a schematic diagram of an automation risk monitor system.
Figure 5:
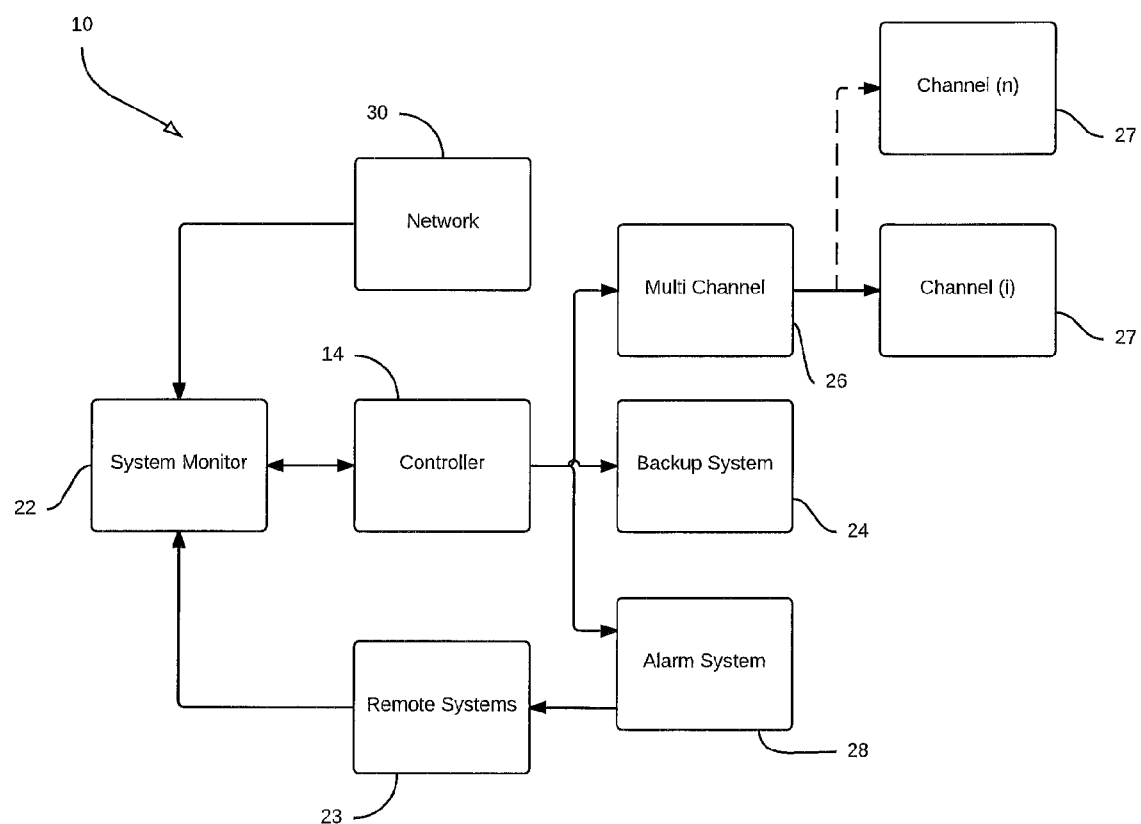
FIG. 5 is a schematic diagram of a closed loop control system augmented with the system monitor of the invention.

FIG. 1 provides a system 10 for monitoring and delivering medication, such as insulin, to a patient 12. The system 10 includes a controller 14 that utilizes a control algorithm and an automation risk monitor 15 all presented in a closed loop. A sensor 16 is in communication with the controller 14 and monitors a medical condition of the patient 12. A rule based application 18 (see FIG. 4 for example) in the automation risk monitor of the controller 14 receives data from the sensor 16 and compares the data to predetermined medical information to determine the risk to the patient 12 to automate the delivery of medication.

The rule based application 18 can be set to assess the therapy being administered and its criticality. Further, the rule based application 18 can assess currently administered drugs and patient 12 characteristics such as food intake, fluid intake, and disease state. Patient physiological response variables such as vitals, labs, and cognitive assessments can also be set to be used by the rule based application 18 to determine the risk to the patient. The rule based application 18 can also be set to include factors related to patient risk parameters such as change in patient state and transitions in therapy such as beginning, continuing, changing, or ending therapy.

The rule based application 18 in one embodiment includes physician or clinician entered conditions of when automation is acceptable. Clinician entered conditions can include therapy importance such as critical, life sustaining, supplementary, and benign. Further, the clinician can establish fail-safe, fail-operate, and fail-stop conditions for infusion that are based on strict rules or based on ranges of conditions. The system 10 is thus in communication with a clinician messaging system 20 that communicates to a clinician when the risk of automation is unacceptable. In a preferred embodiment the messaging system is remote from the system 10.

The rule based application 18 in one embodiment can include a risk profile wherein a clinician implements a risk profile according to a metric that may be qualitative (low, medium or high) or quantitative (1-10 where 10 is the highest risk) and a threshold defining when intervention is required. In either case, a quantitative metric is internally calculated and compared to a quantitative threshold. For example, in the case of low, medium or high each qualitative measurement is assigned a quantitative value such as 2, 5 and 7 respectively. Consequently, a risk scale is specified and a threshold above which intervention is requested. The rule based application 18 can also include a risk matrix that is developed to enable a determination of risk. Although the matrix is ultimately stored internally, it can be parameterized by the user. One example of the risk matrix is shown below:

| Glucose Range (mg/dL) | Glucose Δ (derivative) | Calculated Δ in Insulin | Risk Level |
|---|---|---|---|
| 0-70 | Increasing | Increasing | High |
| 0-70 | Increasing | Decreasing | Low |
| 0-70 | Decreasing | Increasing | High |
| 0-70 | Decreasing | Decreasing | Low |

-continued

| Glucose Range (mg/dL) | Glucose Δ (derivative) | Calculated Δ in Insulin | Risk Level |
|---|---|---|---|
| 70-90 | Increasing | Increasing | Medium |
| 70-90 | Increasing | Decreasing | Low |
| 70-90 | Decreasing | Increasing | High |
| 70-90 | Decreasing | Decreasing | Low |
| 90-120 | Increasing | Increasing | Medium |
| 90-120 | Increasing | Decreasing | Low |
| 90-120 | Decreasing | Increasing | High |
| 90-120 | Decreasing | Decreasing | Low |
| 120-180 | Increasing | Increasing | Low |
| 120-180 | Increasing | Decreasing | Low |
| 120-180 | Decreasing | Increasing | Medium |
| 120-180 | Decreasing | Decreasing | Low |
| 180-250 | Increasing | Increasing | Low |
| 180-250 | Increasing | Decreasing | High |
| 180-250 | Decreasing | Increasing | Medium |
| 180-250 | Decreasing | Decreasing | Low |
| Above 250 | Increasing | Increasing | High |
| Above 250 | Increasing | Decreasing | Low |
| Above 250 | Decreasing | Increasing | Low |
| Above 250 | Decreasing | Decreasing | Medium |

Specifically, the second column is the calculated or requested insulin level from the closed loop controller. The table is an example of how the treatment condition is mapped to a risk level. There are numerous other methods for implementing this information which may include continuous mapping functions, fuzzy logic, probability calculations and the like.

A second way to provide this type of system is to employ an insulin/glucose pharmacokinetic/pharmacodynamic model as shown below which predicts the future glucose level. The clinician can then use a predicted value rather than or in addition to glucose level and a derivative.

$$\dot{G}(t) = -p_G \cdot G(t) - S_I(t) \cdot G \cdot \frac{Q(t)}{1+\alpha_G Q(t)} + \frac{P(t)+EGP-CNS}{V_G}$$

$$\dot{I}(t) = -n\frac{I(t)}{1+\alpha_I I(t)} + \frac{u_{ex}(t)}{V_I} + \frac{u_{en}(t)}{V_I}$$

$$\dot{P}_1(t) = -d_1 P_1(t) + P_e(t)$$

$$\dot{P}_2(t) = -\min(d_2 P_2(t), P_{max}) + d_1 P_1(t)$$

$$P(t) = \min(d_2 P_2(t), P_{max}) + P_N(t)$$

$$\dot{G}(t) = -p_G(t)G(t) - S_I(t)G(t)\frac{Q(t)}{1+\alpha_G Q(t)} + \frac{P(t)}{V_G} \quad (1)$$

$$\dot{Q}(t) = -kQ(t) + kI(t) \quad (2)$$

$$\dot{I}(t) = -n\frac{I(t)}{1+\alpha_I I(t)} + \frac{u_{ex}(t)}{V_I} \quad (3)$$

In Equations (1)-(3), G(t) [mmol/L] denotes the total plasma glucose concentration, and I(t) [mU/L] is the plasma insulin concentration. The effect of previously infused insulin being utilized over time is represented by Q(t) [mU/L], with k [1/min] accounting for the effective life of insulin in the system. Exogenous insulin infusion rate is represented by $u_{ex}$(t) [mU/min], whereas P(t) [mmol/L min] is the exogenous glucose infusion rate. Patient's endogenous glucose removal and insulin sensitivity through time are described by $p_G$(t) [1/min] and $S_I$(t) [L/mU min], respectively. The parameters $V_I$ [L] and $V_G$ [L] stand for insulin and glucose distribution volumes. n [1/min] is the first order decay rate of insulin from plasma. Two Michaelis-Menten constants are used to describe saturation, with $\alpha_I$ [L/mU] used for the saturation of plasma insulin disappearance, and $\alpha_G$ [L/mU] for the saturation of insulin-dependent glucose clearance.

Thus, the rule based application 18 determines the risk to a patient 12 by determining a predetermined risk threshold. Below the predetermined risk threshold, because low risk is detected, the system 10 can move forward in an automated fashion and provide medication as required. If the risk is determined to be above the predetermined risk threshold the controller triggers a request for user intervention by contacting the clinician messaging system 20 instead of moving forward with automation.

The system 10 can also be used to monitor any form of infusion including anti-coagulation monitoring during heparin infusion, respiratory monitoring during pain medication infusion such as morphine, and hemodynamic monitoring during infusion of vaso-active medication for cardio vascular support.

As best understood in view of FIGS. 1-5, in an alternative embodiment the system 10 includes a system monitor 22 that is in communication with the controller 14. In one arrangement the system monitor 22 tracks network activity on a network 30 to determine whether a network failure has occurred. The system 22 also detects interruptions in communication with decision support provided by a remote system 23. Similarly, the system monitor 22 tracks network activity to determine whether an interruption has occurred between the system 10 and the clinician messaging system 20 or other remote system 23 that allows for remote operation of the system 10 by a clinician or other basis of support such as medical record tracking. In the event that an interruption is detected the system 10 is enabled to continue infusion at either a backup infusion rate set by a clinician or the rule based application 18. Alternatively, the system 10 can be configured to set an infusion rate based on a default setting that can include a minimum or maximum rate that depends on the physiological state of the patient 12 and the therapy being administered.

In another embodiment the system monitor 22 detects air in line levels. In this embodiment the system monitor 22 determines whether the amount of air present in line is at a critical level that requires stopping the infusion. When air in line is detected the system monitor 22 sends data to the controller 14 that uses the automation risk monitor 15 to determine whether the criticality of treatment is sufficient to allow the system 10 to continue to operate. In one arrangement, when air is detected by the system monitor 22 an alarm is sent via the clinician messaging system 20 or emitted from the system 10 locally. The system monitor 22 also determines whether the detection of air in line is a false positive and if a false positive is detected the alarm is auto-cleared. The system monitor 22 can also be set to not send an alarm if the amount of air present is non-critical.

Additionally, the system monitor 22 detects whether an occlusion is present. If an occlusion is detected the system monitor 22 sends data to the controller 14 to determine whether the occlusion poses a sufficient risk to adjust the infusion rate. Alternatively, if the controller 14 determines a sufficient risk is presented by an occlusion an alarm can be triggered or a message can be sent via the clinician messaging system 20. In one arrangement the presence of occlusions is based on occlusion pressure levels.

In the event that the system monitor 22 detects a sufficient amount of air or large enough occlusion the system 10 can activate a backup system 24. For example, in a life-sustaining situation, a backup system 24 would be enabled and the infusion rate set by the controller 14. In one arrangement, the backup system 24 maintains infusion parameters set by the system 10 so that treatment can be transitioned without interruption.

In another arrangement the system 10 includes a multi-channel infusion system 26 that allows for multiple treatment paths or channels 27. When the system monitor 22 detects that one channel 27 has failed the system 10 switches to an alternative channel 27 to deliver the infusion. In one embodiment the system 10 adjusts the infusion rate of a concurrently infused medication to compensate for the failure of a channel 27. For example, if a dextrose infusion fails in a hypoglycemic patient 12 the system 10 can increase the infusion of nutrition to compensate for the lack of dextrose being infused.

In one embodiment, the system monitor 22 tracks whether input is received from clinicians after the clinician is contacted via the clinician monitoring system 20 to input or confirm a therapy adjustment. If the clinician fails to respond the system monitor 22 sends data to the controller 14 to adjust treatment based on information from the automation risk monitor 15 as described previously.

An alarm system 28 can also be included in the system 10. The alarm system 28 determines the appropriate alarm to send depending on the level of patient risk, uncertainty, and predicted outcomes. In this manner, the alarm system 28 provides the highest degree of alarm in association with critical events that require immediate attention.

In operation, the system 10 monitors a control algorithm of a controller 14 to receive data. The controller 14 additionally receives continuous data from a sensor 16 regarding a medical condition such as a glucose level. The controller 14 then compares the data from the control algorithm and the sensor 16 to predetermined medical information so that the controller 14 can determine a predetermined risk threshold of automating the delivery of medication. Then, based on the data, if a risk is below a predetermined threshold, automation is permitted and a command or request for medication or insulin is provided to the insulin pump. Therefore the insulin delivery rate is automatically updated according to the algorithm model or closed loop controller used. Alternatively, if the risk is at or above a predetermined threshold a request for user intervention is triggered sending a message to the clinician messaging system 20 so that a user may intervene to make a determination regarding whether the medication should be provided. The request for intervention is generated and sent directly to the user through a messaging system that is bi-directional. The message system 20 provides information and requests a user response. When the response is related to a change in therapy an authentication step is included.

The response to a request is provided by the user directly through the user interface of the system. Alternatively, the response can be returned through an authenticated messaging system involving a unique identifier specific to a positive or negative response. In the event that the clinician fails to respond the therapy may be continued at a lower rate or stopped altogether. Optionally, an alarm can be generated by the alarm system 28.

During the course of normal operation glucose measurements may be received that generate a change in the recommended insulin. However, the change may not be significant enough to provide a therapeutic advantage to the patient versus the burden of requesting confirmation from the nurse. Consequently, a rule based application 18 is provided which evaluates therapy changes to trigger a request for an automatic update or nursing intervention. The input to the rule based application 18 includes the blood glucose level, the change in glucose, the insulin infusion, the recommended change in insulin infusion, the estimated insulin on board, and the predicted glucose in the future. Rules involving comparisons to thresholds, regression equations, and calculations are created which trigger a therapy update based on the inputs.

In the event that an interruption to the normal operation of the system 10, the remote systems 23, or network 30 is detected by the system monitor 22, the system adjusts therapy by altering the infusion rate of the system 10 or switching to a backup system 24. Additionally, if an interruption is detected in a system 10 using multi-channel infusions 26, the system 10 can alter the infusion rate or channel 27 used for infusing to compensate for the channel 27 failure.

When a command request is made or an interruption to normal operation is detected an alarm system 28 determines the appropriate alarm to send. The highest alarm is sent by the alarm system 28 based on the most critical failures of the system 10 or risks to the patient 12.

Thus, the present system can be used to make determinations of treatment decisions requiring user intervention based upon a diagnostic value, the change in diagnostic value, the current drug infusion rate, the updated drug infusion rate, the treatment target range, network failures, system failures, and clinician inactivity. In addition, the system notifies a clinician that intervention is required and receives the implementing clinician instruction in response to the notification.

An additional advantage is presented because the system 10 determines when clinician intervention is necessary and unnecessary. Specifically, system 10 is independent of an adaptive control algorithm or a computerized protocol. The system 10 functions as a supervisor that watches the performance of the closed loop system. Consequently, data from the closed loop system and diagnostic sensor 16 are provided to the rule based application 18 that uses a matrix to produce a quantitative level of risk. The level of risk can be expressed as a discrete general level such as the "High", "Low" and "Medium" values expressed in the table above or the level of risk can be a numerical value, score, index or percentage. The risk is compared to a particular risk threshold to either generate and/or provide an "okay" to proceed with therapy or to trigger a request for user intervention.

This operation differs from current systems that do not determine risk of automation. Instead prior art systems allow automation to occur regardless of potential risk and then when sensors indicate a patient is experiencing an unacceptable medical condition a clinician is alerted. Therefore the system 10 provides an advantage of preventing the unacceptable medical condition from occurring in the first place as a result of monitoring the automation process and pre-determining risks of automation.

A further advantage is found in that the system 10 detects failures of the system 10, remote systems 23, networks 30, and inactivity of clinicians. Upon detection of one of these failures or risks posed to a patient the alarm system 28 escalates alarms based on the risk or risks posed to the patient 12 based on changes to the patient 12 or the system 10. Thus, at the very least all of the stated objectives have been met.

What is claimed is:

1. A system for delivering medication to a patient, the system comprising:
   a controller having a control algorithm and an automation risk monitor that monitors the control algorithm;

a sensor in communication with the controller and the automation risk monitor and monitoring a medical condition;
a rule based application in the automation risk monitor that receives data from the sensor and a closed loop control and compares the data to predetermined medical information to determine risk to a patient;
a network; and
a supervisory system monitor in communication with a remote system, the network, the controller and the automation risk monitor.

2. The system of claim 1 wherein the system monitor detects occlusion pressure levels.

3. The system of claim 1 wherein the system monitor detects air in line levels.

4. A system for delivering medication to a patient, the system comprising:
a controller having a control algorithm and an automation risk monitor that monitors the control algorithm;
a sensor in communication with the controller and the automation risk monitor and monitoring a medical condition;
a rule based application in the automation risk monitor that receives data from the sensor and a closed loop control and compares the data to predetermined medical information to determine risk to a patient; and
a system monitor in communication with a network, the controller and the automation risk monitor:
wherein the system monitor detects network failures.

5. A system for delivering medication to a patient, the system comprising:
a controller having a control algorithm and an automation risk monitor that monitors the control algorithm;
a sensor in communication with the controller and the automation risk monitor and monitoring a medical condition;
a rule based application in the automation risk monitor that receives data from the sensor and a closed loop control and compares the data to predetermined medical information to determine risk to a patient; and
a system monitor in communication with a remote system, the controller and the automation risk monitor;
wherein the system monitor detects remote system failures.

6. The system of claim 1 wherein the controller controls a medication delivery device to deliver medication to the patient based on a comparison of the risk to predetermined risk threshold.

7. A system for delivering medication to a patient, the system comprising:
a controller having a control algorithm and an automation risk monitor that monitors the control algorithm;
a sensor in communication with the controller and the automation risk monitor and monitoring a medical condition;
a rule based application in the automation risk monitor that receives data from the sensor and a closed loop control and compares the data to predetermined medical information to determine risk to a patient; and
a system monitor in communication with the controller and the automation risk monitor;
wherein the controller transitions a medication delivery device to a backup system to deliver medication to the patient based on a comparison of the risk to predetermined risk threshold.

8. A system for delivering medication to a patient, the system comprising:
a controller having a control algorithm and an automation risk monitor that monitors the control algorithm;
a sensor in communication with the controller and the automation risk monitor and monitoring a medical condition;
a rule based application in the automation risk monitor that receives data from the sensor and a closed loop control and compares the data to predetermined medical information to determine risk to a patient;
a multi-channel infusion system; and
a system monitor in communication with the controller and the automation risk monitor;
wherein when the system monitor detects a system failure the controller transitions medication delivery to a different channel of the multi-channel infusion system.

9. A system for delivering medication to a patient, the system comprising:
a controller having a control algorithm and an automation risk monitor that monitors the control algorithm;
a sensor in communication with the controller and the automation risk monitor and monitoring a medical condition;
a rule based application in the automation risk monitor that receives data from the sensor and a closed loop control and compares the data to predetermined medical information to determine risk to a patient;
a multi-channel infusion system; and
a system monitor in communication with the controller and the automation risk monitor;
wherein when the system monitor detects a system failure the controller adjusts a concurrently administered infusion to compensate for the failure.

10. A system for delivering medication to a patient, the system comprising:
a controller having a control algorithm and an automation risk monitor that monitors the control algorithm;
a sensor in communication with the controller and the automation risk monitor and monitoring a medical condition;
a rule based application in the automation risk monitor that receives data from the sensor and a closed loop control and compares the data to predetermined medical information to determine risk to a patient; and
a system monitor in communication with the controller and the automation risk monitor;
wherein the system monitor detects a failure of a clinician to respond.

11. A system for delivering medication to a patient, the system comprising:
a controller having a control algorithm and an automation risk monitor that monitors the control algorithm;
a sensor in communication with the controller and the automation risk monitor and monitoring a medical condition;
a rule based application in the automation risk monitor that receives data from the sensor and a closed loop control and compares the data to predetermined medical information to determine risk to a patient; and
a system monitor in communication with the controller and the automation risk monitor; and
an alarm system that escalates alarms based on the risk to the patient.

12. The system of claim 11 wherein the risk to the patient is determined by the automation risk monitor based on data from the sensor and the system monitor.

13. The system of claim 1 A system for delivering medication to a patient, the system comprising:

a controller having a control algorithm and an automation risk monitor that monitors the control algorithm;

a sensor in communication with the controller and the automation risk monitor and monitoring a medical condition;

a rule based application in the automation risk monitor that receives data from the sensor and a closed loop control and compares the data to predetermined medical information to determine risk to a patient; and a system monitor in communication with a remote system, the controller and the automation risk monitor;

wherein the system monitor monitors remote system activity.

14. A system for delivering medication to a patient, the system comprising:

a controller having a control algorithm and an automation risk monitor that monitors the control algorithm;

a sensor in communication with the controller and the automation risk monitor and monitoring a medical condition;

a rule based application in the automation risk monitor that receives data from the sensor and a closed loop control and compares the data to predetermined medical information to determine risk to a patient; and a system monitor in communication with a network, the controller and the automation risk monitor:

wherein the system monitor monitors network activity.

* * * * *